ions Patent [19]
Takaya et al.

[11] Patent Number: 4,463,003
[45] Date of Patent: Jul. 31, 1984

[54] CEPHEM COMPOUNDS

[75] Inventors: Takao Takaya, Kawanishi; Hisashi Takasugi, Osaka; Hideaki Yamanaka, Hirakata, all of Japan

[73] Assignee: Fujisawa Pharmaceutical Co., Ltd., Osaka, Japan

[21] Appl. No.: 452,302

[22] Filed: Dec. 22, 1982

[51] Int. Cl.³ .............. A61K 31/545; C07D 501/34; C07D 501/56
[52] U.S. Cl. ............................ 424/246; 544/27; 544/28
[58] Field of Search ............... 424/246; 544/27, 28

[56] References Cited

U.S. PATENT DOCUMENTS 4,064,346 12/1977 Cook et al. .................... 424/246
4,263,291 4/1981 Takaya et al. ................. 424/246
4,332,798 6/1982 Teraji et al. ................... 424/246

FOREIGN PATENT DOCUMENTS

57422A2 8/1982 European Pat. Off. .

Primary Examiner—Paul M. Coughlan, Jr.
Attorney, Agent, or Firm—Oblon, Fisher, Spivak, McClelland & Maier

[57] ABSTRACT

The invention relates to novel cephem compounds, of antimicrobial activity, of the formula:

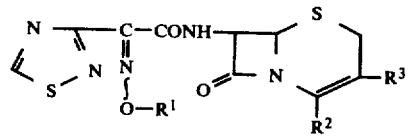

wherein $R^1$ is carboxy ($C_1$–$C_6$) alkyl or esterified carboxy ($C_1$–$C_6$) alkyl, $R^2$ is carboxy or esterified carboxy, and $R^3$ is ($C_1$–$C_6$) alkanoyloxy ($C_1$–$C_6$) alkyl, tetrazolopyridazinylthio ($C_1$–$C_6$) alkyl, tetrazolothio ($C_1$–$C_6$) alkyl, or ($C_1$–$C_6$) alkyl tetrazolothio ($C_1$–$C_6$) alkyl, and pharmaceutically acceptable salts thereof.

5 Claims, No Drawings

CEPHEM COMPOUNDS

The present invention relates to new cephem compounds and pharmaceutically acceptable salts thereof. More particularly, it relates to new cephem compounds and pharmaceutically acceptable salts thereof, which have antimicrobial activities, to processes for preparation thereof, to pharmaceutical composition comprising the same, and to a method of using the same therapeutically in the treatment of infectious diseases in human being and animals.

Accordingly, it is one object of the present invention to provide new cephem compounds and pharmaceutically acceptable salts thereof, which are active against a number of pathogenic microorganisms, especially for oral administration.

Another object of the present invention is to provide processes for the preparation of new cephem compounds and pharmaceutically acceptable salts thereof.

A further object of the present invention is to provide pharmaceutical composition comprising, as active ingredients, said new cephem compounds and pharmaceutically acceptable salts thereof.

Still further object of the present invention is to provide a method for the treatment of infectious diseases caused by pathogenic bacteria in human being and animals.

The object new cephem compounds are novel and can be represented by the following general formula:

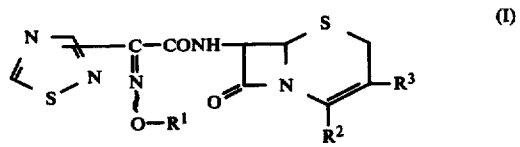

wherein
R$^1$ is carboxy(lower)alkyl or protected carboxy(lower)alkyl,
R$^2$ is carboxy or protected carboxy, and
R$^3$ is acyloxy(lower)alkyl, or heterocyclicthio(lower)alkyl which may have suitable substituent(s).

According to the present invention, the new cephem compounds (I) can be prepared by various processes which are illustrated in the following schemes.

Process 1

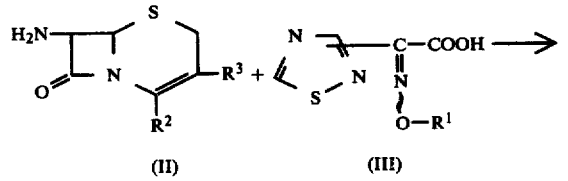

(II)
or its reactive derivative at the amino group or a salt thereof (III)
or its reactive derivative at the carboxy group or a salt thereof

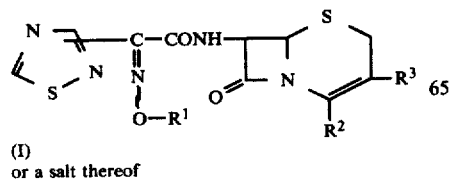

(I)
or a salt thereof

Process 2

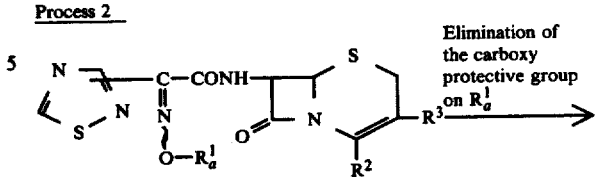

(Ia)
or a salt thereof

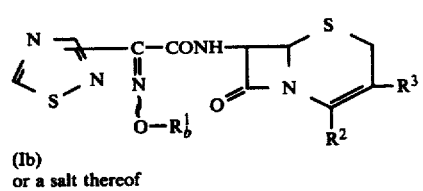

(Ib)
or a salt thereof wherein
R$^1$, R$^2$ and R$^3$ are each as defined above,
R$_a{}^1$ is protected carboxy(lower)alkyl, and
R$_b{}^1$ is carboxy(lower)alkyl.

In the present invention, with regard to the object compounds (I) and (Ib), the starting compounds (Ia) and (III), it is to be understood that all of said compounds include syn isomer, anti isomer and a mixture thereof. And, as to the object compounds (I), the syn isomer thereof means one geometrical isomer having the group represented by the following formula:

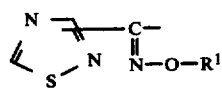

(wherein R$^1$ is as defined above)
and the anti isomer means the other geometrical isomer having the group of the formula:

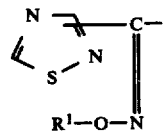

(wherein R$^1$ is as defined above)
Further, as to the other compounds, the syn and anti isomers thereof also are represented by the same geometrical configuration as that of the object compound (I), respectively.

Suitable pharmaceutically acceptable salts of the object compounds (I) are conventional non-toxic salts and may include an inorganic salt, for example, a metal salt such as an alkali metal salt (e.g., sodium salt, potassium salt, etc.) and an alkaline earth metal salt (e.g., calcium salt, magnesium salt, etc.), ammonium salt, etc.;

an organic salt, for example, an organic amine salt (e.g., trimethylamine salt, triethylamine salt, pyridine salt, procaine salt, picoline salt, dicyclohexylamine salt, N,N'-dibenzylethylene-diamine salt, N-methylglucamine salt, diethanolamine salt, triethanolamine salt, tris(hydroxymethylamino)methane salt, phenylethylbenzylamine salt, dibenzylethylenediamine salt, etc.) etc.;

an organic carboxylic or sulfonic acid salt (e.g., formate, acetate, maleate, tartrate, methanesulfonate, benzenesulfonate, toluenesulfonate, etc.); an inorganic acid salt (e.g., hydrochloride, hydrobromide, sulfate, phosphate, etc.);

a salt with a basic or acidic amino acid (e.g., arginine, aspartic acid, glutamic acid, lysine, etc.) and the like.

In the above and subsequent descriptions of the present specification, suitable examples and illustrations of the various definitions which the present invention include within the scope thereof are explained in details as follows.

The term "lower" is intended to mean 1 to 6 carbon atoms, unless otherwise indicated.

Suitable "protected carboxy" and "protected carboxy moiety" in the term "protected carboxy(lower)alkyl" may include an esterified carboxy, and suitable examples of the ester moiety in said esterified carboxy may be the ones such as lower alkyl ester (e.g. methyl ester, ethyl ester, propyl ester, isopropyl ester, butyl ester, isobutyl ester, tert-butyl ester, pentyl ester, hexyl ester, 1-cyclopropylethyl ester, etc.) which may have at least one suitable substituent(s), for example, lower alkanoyloxy(lower)alkyl ester (e.g. acetoxymethyl ester, propionyloxymethyl ester, butyryloxymethyl ester, valeryloxymethyl ester, pivaloyloxymethyl ester, 2-acetoxyethyl ester, 2-propionyloxyethyl ester, hexanoyloxymethyl ester, etc.), lower alkanesulfonyl(lower)alkyl ester (e.g. 2-mesylethyl ester, etc.) or mono(or di or tri)-halo(lower)alkyl ester (e.g. 2-iodoethyl ester, 2,2,2-trichloroethyl ester, etc.); lower alkenyl ester (e.g. vinyl ester, allyl ester, etc.);

lower alkynyl ester (e.g. etynyl ester, propynyl ester, etc.);

ar(lower)alkyl ester which may have at least one suitable substituent(s) (e.g. benzyl ester, 4-methoxybenzyl ester, 4-nitrobenzyl ester, phenethyl ester, trityl ester, benzhydryl ester, bis(methoxyphenyl)methyl ester, 3,4-dimethoxybenzyl ester, 4-hydroxy-3,5-di-tert-butylbenzyl ester, etc.);

aryl ester which may have at least one suitable substituent(s) (e.g. phenyl ester, 4-chlorophenyl ester, tolyl ester, tert-butylphenyl ester, xylyl ester, mesityl ester, cumenyl ester, etc.).

Preferable example of protected carboxy may include lower alkoxycarbonyl (e.g. methoxycarbonyl, ethoxycarbonyl, propoxycarbonyl, isopropoxycarbonyl, butoxycarbonyl, isobutoxycarbonyl, tert-butoxycarbonyl, pentyloxycarbonyl, tert-pentyloxycarbonyl, hexyloxycarbonyl, 1-cyclopropylethoxycarbonyl, etc.), and the like.

Suitable "lower alkyl moiety" in the terms "carboxy(lower)alkyl", "protected carboxy(lower)alkyl", "acyloxy(lower)alkyl" and "heterocyclicthio(lower)alkyl which may have suitable substituent(s)" may include methyl, ethyl, propyl, isopropyl, butyl, t-butyl, pentyl, and hexyl.

Suitable "acyl moiety" in the term "acyloxy(lower)alkyl" may include lower alkanoyl (e.g., formyl, acetyl, propionyl, butyryl, isobutyryl, valeryl, isovaleryl, oxalyl, succinyl, pivaloyl, etc.), preferably one having 1 to 4 carbon atom(s), more preferably one having 1 to 2 carbon atom(s); lower alkoxycarbonyl having 2 to 7 carbon atoms (e.g., methoxycarbonyl, ethoxycarbonyl, propoxycarbonyl, 1-cyclopropylethoxycarbonyl, isopropoxycarbonyl, butoxycarbonyl, t-butoxycarbonyl, pentyloxycarbonyl, t-pentyloxycarbonyl, hexyloxycarbonyl, etc.), preferably one having 3 to 6 carbon atoms; lower alkanesulfonyl (e.g., mesyl, ethanesulfonyl, propanesulfonyl, isopropanesulfonyl, butanesulfonyl, etc.);

arenesulfonyl (e.g., benzenesulfonyl, tosyl, etc.); aroyl (e.g., benzoyl, toluoyl, naphthoyl, phthaloyl, indancarbonyl, etc.);

ar(lower)alkanoyl (e.g., phenylacetyl, phenylpropionyl, etc.); cyclo(lower)alkyl(lower)alkanoyl (e.g. cyclohexylacetyl, cyclopentylacetyl, etc.);

ar(lower)alkoxycarbonyl (e.g. benzyloxycarbonyl, phenethyloxycarbonyl, etc.).

Suitable "heterocyclic moiety" in the term "heterocyclicthio(lower)alkyl which may have suitable substituent(s)" means saturated or unsaturated, monocyclic or polycyclic heterocyclic group containing at least one hetero-atom such as an oxygen, sulfur, nitrogen atom and the like. And, especially preferably heterocyclic group may be heterocyclic group such as unsaturated 3 to 8-membered heteromonocyclic group containing 1 to 4 nitrogen atom(s), for example, pyrrolyl, pyrrolinyl, imidazolyl, pyrazolyl, pyridyl, and its N-oxide, pyrimidyl, pyrazinyl, pyridazinyl, triazolyl (e.g., 4H-1,2,4-triazolyl, 1H-1,2,3-triazolyl, 2H-1,2,3-triazolyl, etc.), tetrazolyl (e.g., 1H-tetrazolyl, 2H-tetrazolyl, etc.), dihydrotriazinyl, etc.;

saturated 3 to 8-membered heteromonocyclic group containing 1 to 4 nitrogen atom(s), for example, pyrrolidinyl, imidazolidinyl, piperidino, piperazinyl, etc.; unsaturated condensed heterocyclic group containing 1 to 5 nitrogen atom(s), for example, indolyl, isoindolyl, indolizynyl, benzimidazolyl, quinolyl, isoquinolyl, indazolyl, benzotriazolyl, tetrazolopyridyl, tetrazolopyridazinyl, (e.g., tetrazolo[1,5-b]pyridazinyl, etc.) dihydrotriazolopyridazinyl, etc.;

unsaturated 3-to 8-membered heteromonocyclic group containing 1 to 2 oxygen atom(s) and 1 to 3 nitrogen atom(s), for example, oxazolyl, isoxazolyl, oxadiazolyl, (e.g., 1,2,4-oxadiazolyl, 1,3,4-oxadiazolyl, 1,2,5-oxadiazolyl, etc.) etc.;

saturated 3 to 8-membered heteromonocyclic group containing 1 to 2 oxygen atom(s) and 1 to 3 nitrogen atom(s), for example, morpholinyl, etc.;

unsaturated condensed heterocyclic group containing 1 to 2 oxygen atom(s) and 1 to 3 nitrogen atom(s), for example, benzoxazolyl, benzoxadiazolyl, etc.;

unsaturated 3 to 8-membered heteromonocyclic group containing 1 to 2 sulfur atom(s) and 1 to 3 nitrogen atom(s), for example, thiazolyl, thiazolinyl, thiadiazolyl (e.g., 1,2,4-thiadiazolyl, 1,3,4-thiadiazolyl, 1,2,5-thiadiazolyl, etc.), etc.;

saturated 3 to 8-membered heteromonocyclic group containing 1 to 2 sulfur atom(s) and 1 to 3 nitrogen atom(s), for example, thiazolidinyl, etc.;

unsaturated 3 to 8-membered heteromonocyclic group containing a sulfur atom, for example, thienyl, etc.; unsaturated condensed heterocyclic group containing 1 to 2 sulfur atom(s) and 1 to 3 nitrogen atom(s), for example, benzothiazolyl, benzothiadiazolyl, etc. and the like.

Suitable substituent in the term "heterocyclicthio(lower)alkyl which may have suitable substituent(s)" may include lower alkyl (e.g., methyl, ethyl, propyl, isopropyl, butyl, isobutyl, pentyl, cyclopentyl, hexyl, cyclohexyl, etc.), and the like.

Preferred embodiments of the object compounds (I) are as follows.

Preferred embodiment of $R^1$ is carboxy(lower)alkyl or esterified carboxy(lower)alkyl[more preferably lower alkoxycarbonyl(lower)alkyl];

$R^2$ is carboxy; and $R^3$ is acyloxy(lower)alkyl[more preferably lower alkanoyloxy(lower)alkyl], unsaturated condensed heterocyclicthio(lower)alkyl containing 1 to 5 nitrogen atom(s) [more preferably tetrazolopyridazinylthio(lower)alkyl, most preferably tetrazolopyridazinylthiomethyl], or unsaturated 3 to 8-membered heteromonocyclicthio(lower)alkyl containing 1 to 4 nitrogen atom(s) which have lower alkyl[more preferably tetrazolylthio(lower)alkyl having lower alkyl, most preferably tetrazolylthiomethyl having lower alkyl].

The processes for preparing the object compounds of the present invention are explained in details in the following.

PROCESS 1

The object compound (I) or a salt thereof can be prepared by reacting the compound (II) or its reactive derivative at the amino group or a salt thereof with the compound (III) or its reactive derivative at the carboxy group or a salt thereof.

Suitable reactive derivative at the amino group of the compound (II) may include Schiff's base type imino or its tautomeric enamine type isomer formed by the reaction of the compound (II) with a carbonyl compound such as aldehyde, ketone or the like; a silyl derivative formed by the reaction of the compound (II) with a silyl compound such as bis(trimethylsilyl)acetamide, trimethylsilylacetamide or the like; a derivative formed by reaction of the compound (II) with phosphorus trichloride or phosgene, and the like.

Suitable salts of the compounds (II) and (III) can be referred to the ones exemplifed for Compound (I).

Suitable reactive derivative at the carboxy group of the compound (III) may include an acid halide, an acid anhydride, an activated amide, an activated ester, and the like. The suitable example may be an acid chloride, an acid azide; a mixed acid anhydride with an acid such as substituted phosphoric acid (e.g. dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, sulfuric acid, alkylcarbonic acid, aliphatic carboxylic acid (e.g. pivalic acid, pentanoic acid, isopentanoic acid, 2-ethylbutyric acid or trichloroacetic acid, etc.) or aromatic carboxylic acid (e.g. benzoic acid, etc.); a symmetrical acid anhydride; an activated amide with imidazole, 4-substituted imidazole, dimethylpyrazole, triazole or tetrazole; or an activated ester (e.g. cyanomethyl ester, methoxymethyl ester, dimethyliminomethyl [(CH$_3$)$_2$N$^+$=CH— ester, vinyl ester, propargyl ester, p-nitrophenyl ester, 2,4-dinitrophenyl ester, trichlorophenyl ester, pentachlorophenyl ester, mesyl phenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.), or an ester with a N-hydroxy compound (e.g. N,N-dimethylhydroxylamine, 1-hydroxy-2-(1H)-pyridone, N-hydroxysuccinimide, N-hydroxyphthalimide, 1-hydroxy-6-chloro-1H-benzotriazole, etc.), and the like. These reactive derivatives can optionally be selected from them according to the kind of the compound (III) to be used.

The reaction is usually carried out in a conventional solvent such as water, acetone, dioxane, acetonitrile, chloroform, methylene chloride, ethylene chloride, tetrahydrofuran, ethyl acetate, N,N-dimethylformamide, pyridine or any other organic solvents which do not adversely influence the reaction. These conventional solvents may also be used in a mixture with water.

When the compound (III) is used in free acid form or its salt form in the reaction, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide; N,N'-diisopropylcarbodiimide; N-ethyl-N'-(3-dimethylaminopropyl)carbodiimide; N,N-carbonylbis-(2-methylimidazole); pentamethyleneketene-N-cyclohexylimine; diphenylketene-N-cyclohexylimine; ethoxyacetylene; 1-alkoxy-1-chloroethylene; trialkyl phosphite; ethyl polyphosphate; isopropyl polyphosphate; phosphorus oxychloride (phosphoryl chloride); phosphorus trichloride; thionyl chloride; oxalyl chloride; triphenylphosphine; 2-ethyl-7-hydroxybenzisoxazolium salt; 2-ethyl-5-(m-sulfophenyl)isoxazolium hydroxide intramolecular salt; 1-(p-chlorobenzenesulfonyloxy)-6-chloro-1H-benzotriazole; so-called Vilsmeier reagent prepared by the reaction of N,N-dimethylformamide with thionyl chloride, phosgene, phosphorus oxychloride, etc.; or the like.

The reaction may also be carried out in the presence of an inorganic or organic base such as an alkali metal bicarbonate, tri(lower)alkylamine, pyridine, N-(lower)alkylmorphorine, N,N-di(lower)alkylbenzylamine, or the like. The reaction temperature is not critical, and the reaction is usually carried out under cooling or at ambient temperature.

PROCESS 2

The object compound (Ib) or a salt thereof can be prepared by subjecting the compound (Ia) or a salt thereof to elimination reaction of the carboxy protective group on $R_a^1$.

Suitable salts of the compounds (Ia) and (Ib) can be referred to the ones exemplified for the compound (I).

The present reaction is carried out in accordance with a conventional method such as hydrolysis, reduction or the like.

In case that the protective group is an ester, the protective group can be eliminated by hydrolysis. Hydrolysis is preferably carried out in the presence of a base or an acid. Suitable base may include an inorganic base and an organic base such as an alkali metal (e.g. sodium, potassium, etc.), an alkaline earth metal (e.g. magnesium, calcium, etc.), the hydroxide or carbonate or bicarbonate thereof, trialkylamine (e.g. trimethylamine, triethylamine, etc.), picoline, 1,5-diazabicyclo[4,3,0]-none-5-ene, 1,4-diazabicyclo[2,2,2]octane, 1,8-diazabicyclo[5,4,0]undecene-7, or the like. Suitable acid may include an organic acid (e.g. formic acid, acetic acid, propionic acid, trifluoroacetic acid, etc.) and an inorganic acid (e.g. hydrochloric acid, hydrobromic acid, sulfuric acid, etc.). The acidic hydrolysis using trifluoroacetic acid is usually accelerated by addition of anisole.

The reaction is usually carried out in a solvent such as water, methylene chloride, an alcohol (e.g. methanol, ethanol, etc.), a mixture thereof or any other solvent which does not adversely influence the reaction. A liquid base or acid can be also used as the solvent. The reaction temperature is not critical and the reaction is usually carried out under cooling to warming.

Reduction can be applied preferably for elimination of the protective group such as 4-nitrobenzyl, 2-iodoethyl, 2,2,2-trichloroethyl, or the like. The reduction method applicable for the elimination reaction may include, for example, reduction by using a combination of a metal (e.g. zinc, zinc amalgam, etc.) or a salt of chrome compound (e.g. chromous chloride, chromous acetate, etc.) and an organic or inorganic acid (e.g. acetic acid, propionic acid, hydrochloric acid, etc.); and conventional catalytic reduction in the presence of a conventional metallic catalyst (e.g. palladium-carbon, etc.).

The object compounds (I) and pharmaceutically acceptable salts thereof of the present invention are novel compounds which exhibit high antibacterial activity and inhibit the growth of a wide variety of pathogenic microorganisms including Gram-positive and Gram-negative bacteria and are useful as antimicrobial agents. For therapeutic purpose, the compounds according to the present invention can be used in the form of conventional pharmaceutical preparation which contain said compounds, as an active ingredient, in admixture with a pharmaceutically acceptable carrier such as an organic or an inorganic solid or liquid excipient suitable for oral, parenteral or external administration. The pharmaceutical preparations may be in solid form such as capsule, tablet, dragee, ointment or suppository, or in liquid form such as solution, suspension, or emulsion. If desired, there may be included in the above preparations auxiliary substances, stabilizing agents, wetting or emulsifying agents, buffers and other commonly used additives such as lactose, fumaric acid, citric acid, tartaric acid, stearic acid, maleic acid, succinic acid, malic acid, magnesium stearate, terra alba, sucrose, corn starch, talc, gelatin, agar, pectin, peanut oil, olive oil, cacao butter, ethylene glycol, and the like.

While the dosage of the compounds will vary depending upon the age and condition of the patient, an average single dose of about 10 mg, 50 mg, 100 mg, 250 mg, 500 mg, and 1000 mg of the compounds according to the present invention was proved to be effective for treating infectious diseases caused by pathogenic bacteria. In general, amount between 1 mg/body and about 6,000 mg/body or even more may be administered per day.

In order to illustrate the usefulness of the object compound, anti-microbial activities, urinary excretion and biliary excretion of a representative compound of the present invention are shown below.

[1] Test Compound:

7-[2-Carboxymethoxyimino-2-(1,2,4-thiadiazol-3-yl)acetamido]-3-tetrazolo[1,5-b]pyridazin-6-yl)thiomethyl-3-cephem-4-carboxylic acid (syn isomer). (hereinafter referred to as compound Ⓐ)

[2] Test:

(A) Minimal inhibitory concentrations
①  Test Method

In vitro antibacterial activity was determined by the two-fold agar-plate dilution method as described below.

One loopful of an overnight culture of each test strain in Trypticase-soy broth ($10^8$ viable cells per ml) was streaked on heart infusion agar (HI-agar) containing graded concentrations of representative test compound, and the minimal inhibitory concentration (MIC) was expressed in terms of μg/ml after incubation at 37° C. for 20 hours.

② Test Results

| Test strains | MIC (μg/ml) Compound Compound Ⓐ |
|---|---|
| Proteus mirabilis 18 | 0.05 |
| Proteus vulgaris 2 | 0.05 |

(B) Urinary excretion
① Test Method

Urine of rats was collected with a urine collector at 0 to 6, and 6 to 24 hours after oral administration of 100 mg/kg of the test antibiotic. The antibiotic levels in the urine samples were bioassayed with the standard solution prepared with M/15 phosphate buffer (pH 7.0) and the urinary recovery in 24 hours was calculated.

② Test Result

| | Urinary recovery in 24 hours (%) |
|---|---|
| Compound Ⓐ | 10.59 |

(C) Biliary excretion
① Test Method

Rats anesthetized with pentobarbital were fixed in supine position, and a polyethylene cannula was inserted into the bile duct. Bile samples were collected at 0 to 3, 3 to 6, and 6 to 24 hours after oral administration of 100 mg/kg of the test antibiotic. The antibiotic levels in the bile samples were bioassayed with the standard solution prepared with M/15 phosphate buffer (pH 7.0) and the biliary recovery in 24 hours were calculated.

② Test Result

| | Biliary recovery in 24 hours (%) |
|---|---|
| Compound Ⓐ | 12.56 |

The following Examples are given for the purpose of illustrating the present invention.

EXAMPLE 1

Vilsmeier reagent was prepared from phosphorus oxychloride (1.4 g) and N,N-dimethylformamide (0.65 g) in ethyl acetate (2.6 ml) in a usual manner. 2-t-Butoxycarbonylmethoxyimino-2-(1,2,4-thiadiazol-3-yl)acetic acid (syn isomer) (2.1 g) was added to the stirred suspension of Vilsmeier reagent in ethyl acetate (20 ml) under ice-cooling and the mixture was stirred for 30 minutes at the same temperature to prepare an activated acid solution. 7-Amino-3-(tetrazolo[1,5-b]pyridazin-6-yl)thiomethyl-3-cephem-4-carboxylic acid (3.0 g) was dissolved to the solution of sodium bicarbonate (2.1 g) in water (25 ml) and acetone (25 ml). To the solution was added the above activated acid solution at −3° to 3° C. and the solution was stirred for 30 minutes under keeping the pH 7 to 8 with 20% an aqueous solution of sodium carbonate. Ethyl acetate and water were added to the reaction mixture and the mixture was adjusted to pH 2.0 with 10% hydrochloric acid. The separated organic layer was washed with saturated aqueous solution of sodium chloride, dried over magnesium sulfate and evaporated to give 7-[2-t-butoxycarbonylmethoxyimino-2-(1,2,4-thiadiazol-3-yl)acetamido]-3-(tetrazolo[1,5-b]pyridazin-6-yl)thiomethyl-3-cephem-4-carboxylic acid (syn isomer) (4.07 g).

IR (Nujol): 1770, 1710, 1680 cm$^{-1}$.

NMR (DMSO-d$_6$, δ): 1.46 (9H, s), 3.77 (2H, m), 4.47 (2H, q, J=14.0 Hz), 4.76 (2H, s), 5.23 (1H, d, J=5.0 Hz), 5.93 (1H, dd, J=5.0 Hz, 8.0 Hz), 7.76 (1H, d, J=10.0 Hz), 8.62 (1H, d, J=10.0 Hz), 9.71 (1H, d, J=8 Hz), 10.34 (1H, s).

EXAMPLE 2

The following compounds were obtained according to a similar manner to that of Example 1.

(1) 7-[2-Carboxymethoxyimino-2-(1,2,4-thiadiazol-3-yl)acetamido]-3-(tetrazolo[1,5-b]pyridazin-6-yl)thiomethyl-3-cephem-4-carboxylic acid (syn isomer).

IR (Nujol): 1770, 1720, 1680 cm$^{-1}$.

(2) 7-[2-t-Butoxycarbonylmethoxyimino-2-(1,2,4-thiadiazol-3-yl)acetamido]cephalosporanic acid (syn isomer).

IR (Nujol): 3250, 1780, 1720, 1540 cm$^{-1}$.

NMR (DMSO-d$_6$, δ): 1.43 (9H, s), 2.02 (3H, s), 3.53 (2H, ABq, J=18 Hz), 4.70 (2H, s), 4.82 (2H, ABq, J=12 Hz), 5.17 (1H, d, J=5 Hz), 5.85 (1H, dd, J=5 Hz, 8 Hz), 9.62 (1H, d, J=8 Hz), 10.23 (1H, s).

(3) 7-[2-Carboxymethoxyimino-2-(1,2,4-thiadiazol-3-yl)acetamido]cephalosporanic acid (syn isomer).

IR (Nujol): 3200, 1780, 1720, 1680, 1540 cm$^{-1}$.

(4) 7-[2-t-Butoxycarbonylmethoxyimino-2-(1,2,4-thiadiazol-3-yl)acetamido]-3-(1-methyl-1H-tetrazol-5-yl)thiomethyl-3-cephem-4-carboxylic acid (syn isomer).

IR (Nujol): 3200, 1780, 1720, 1680, 1620, 1530 cm$^{-1}$.

NMR (DMSO-d$_6$, δ): 1.37 (9H, s), 3.62 (2H, broad s), 3.85 (3H, s), 4.25 (2H, ABq, J=13 Hz), 4.65 (2H, s), 5.08 (1H, d, J=5 Hz), 5.77 (1H, dd, J=5 Hz, 8 Hz), 9.58 (1H, d, J=8 Hz), 10.18 (1H, s).

(5) 7-[2-Carboxymethoxyimino-2-(1,2,4-thiadiazol-3-yl)acetamido]-3-(1-methyl-1H-tetrazol-5-yl)thiomethyl-3-cephem-4-carboxylic acid (syn isomer).

IR (Nujol): 3200, 1700, 1680, 1620, 1540 cm$^{-1}$.

EXAMPLE 3

Trifluoroacetic acid (12 ml) was added to a suspension of 7-[2-t-butoxycarbonylmethoxyimino-2-(1,2,4-thiadiazol-3-yl)acetamido]-3-(tetrazolo[1,5-b]pyridazin-6-yl)thiomethyl-3-cephem-4-carboxylic acid (syn isomer) (4 g) in methylene chloride (8 ml) and anisole (4 ml) at ambient temperature and the solution was stirred for 1.5 hours at the same temperature. To the resulting solution was added diisopropyl ether under stirring. The precipitates were collected by filtration, washed with diisopropyl ether. The precipitates were added to the mixture of ethyl acetate and water, and the mixture was adjusted to pH 7.5 with 20% aqueous solution of sodium carbonate. The separated aqueous layer was adjusted to pH 5.0 with 10% hydrochloric acid. The resulting solution was subjected to column chromatography on macroporous non-ionic adsorption resin "Diaion HP-20" (Trademark: prepared by Mitsubishi Chemical Industries Ltd.) and eluted with water. The fractions containing the object compound were adjusted to pH 2.0 with 10% hydrochloric acid. The precipitates were collected by filtration, washed with water and dried over phosphorus pentoxide in vacuo to give 7-[2-carboxymethoxyimino-2-(1,2,4-thiadiazol-3-yl)acetamido]3-(tetrazolo[1,5-b]pyridazin-6-yl)thiomethyl-3-cephem-4-carboxylic acid (syn isomer) (0.77 g).

IR (Nujol): 1770, 1720, 1680 cm$^{-1}$.

NMR (DMSO-d$_6$, δ): 3.74 (2H, q, J=18.0 Hz), 8.61 (1H, d, J=10.0 Hz), 4.45 (2H, q, J=14.0 Hz), 9.73 (1H, d, J=8.0 Hz), 4.77 (2H, s), 10.34 (1H, s), 5.22 (1H, d, J=5.0 Hz), 5.94 (1H, dd, J=5.0 Hz, 8.0 Hz), 7.78 (1H, d, J=10.0 Hz).

EXAMPLE 4

The following compounds were obtained according to a similar manner to that of Example 3.

(1) 7-[2-Carboxymethoxyimino-2-(1,2,4-thiadiazol-3-yl)acetamido]cephalosporanic acid (syn isomer).

IR (Nujol): 3200, 1780, 1720, 1680, 1540 cm$^{-1}$.

NMR (DMSO-d$_6$, δ): 2.03 (3H, s), 3.57 (2H, broad s), 4.77 (2H, s), 4.85 (2H, ABq, J=13 Hz), 5.18 (1H, d, J=5 Hz), 5.88 (1H, dd, J=5 Hz, 8 Hz), 9.63 (1H, d, J=8 Hz), 10.25 (1H, s).

(2) 7-[2-Carboxymethoxyimino-2-(1,2,4-thiadiazol-3-yl)acetamido]-3-(1-methyl-1H-tetrazol-5-yl)thiomethyl-3-cephem-4-carboxylic acid (syn isomer).

IR (Nujol): 3200, 1770, 1680, 1620, 1540 cm$^{-1}$.

NMR (DMSO-d$_6$, δ): 3.67 (2H, broad s), 3.93 (3H, s), 4.27 (2H, ABq, J=13 Hz), 4.73 (2H, s), 5.12 (1H, d, J=5 Hz), 5.82 (1H, dd, J=5 Hz, 8 Hz), 9.62 (1H, d, J=8 Hz), 10.20 (1H, s).

What we claim is:

1. A compound of the formula:

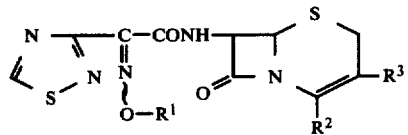

wherein
  $R^1$ is carboxy ($C_1$-$C_6$) alkyl or esterified carboxy ($C_1$-$C_6$) alkyl,
  $R^2$ is carboxy or esterified carboxy, and
  $R^3$ is ($C_1$-$C_6$) alkanoyloxy ($C_1$-$C_6$) alkyl, tetrazolopyridazinylthio ($C_1$-$C_6$) alkyl, tetrazolothio ($C_1$-$C_6$) alkyl, or ($C_1$-$C_6$) alkyl tetrazolothio ($C_1$-$C_6$) alkyl,
and pharmaceutically acceptable salts thereof.

2. A compound of claim 1, which is 7-[2-carboxymethoxyimino-2-(1,2,4-thiadiazol-3-yl)acetamido]-3-(tetrazolo[1,5-b]pyridazin-6-yl)thiomethyl-3-cephem-4-carboxylic acid (syn isomer).

3. A compound of claim 1, which is 7-[2-carboxymethoxyimino-2-(1,2,4-thiadiazol-3-yl)acetamido]cephalosporanic acid (syn isomer).

4. A compound of claim 1, which is 7-[2-carboxymethoxyimino-2-(1,2,4-thiadiazol-3-yl)acetamido]-3-(1-methyl-1H-tetrazol-5-yl)thiomethyl-3-cephem-4-carboxylic acid (syn isomer).

5. An antibacterial composition comprising an effective of a compound of claim 1 in association with a pharmaceutically acceptable substantially non-toxic carrier or excipient.

* * * * *